(12) United States Patent
Davis et al.

(10) Patent No.: US 8,622,967 B2
(45) Date of Patent: Jan. 7, 2014

(54) OVER-THE-NEEDLE INTRAVENOUS CATHETER ASSEMBLY WITH INTEGRATED INTRAVENOUS TUBING

(75) Inventors: Bryan G. Davis, Sandy, UT (US); Bart D. Peterson, Farmington, UT (US); Bryan Fred Bihlmaier, Provo, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 13/471,701

(22) Filed: May 15, 2012

(65) Prior Publication Data

US 2013/0310751 A1    Nov. 21, 2013

(51) Int. Cl.
*A61M 5/178*    (2006.01)

(52) U.S. Cl.
USPC ............ 604/164.01; 604/164.12; 604/167.02; 604/537

(58) Field of Classification Search
USPC ......... 604/82, 164.01–170.03, 174, 175, 518, 604/537
See application file for complete search history.

(56) References Cited

U.S. PATENT DOCUMENTS

| | | | |
|---|---|---|---|
| 4,935,010 A * | 6/1990 | Cox et al. ....................... 604/122 |
| 5,085,645 A * | 2/1992 | Purdy et al. ............... 604/167.03 |
| 5,531,720 A * | 7/1996 | Atkins ........................... 604/537 |
| 5,545,146 A * | 8/1996 | Ishak ............................. 604/198 |
| 5,749,857 A * | 5/1998 | Cuppy ...................... 604/164.12 |
| 5,843,046 A * | 12/1998 | Motisi et al. ................... 604/256 |
| 5,967,490 A * | 10/1999 | Pike ............................ 251/149.1 |
| 7,125,396 B2 * | 10/2006 | Leinsing et al. .......... 604/167.03 |
| 8,105,288 B2 * | 1/2012 | Keyser et al. ............... 604/164.1 |
| 2004/0199141 A1* | 10/2004 | Altman .......................... 604/507 |
| 2010/0204675 A1* | 8/2010 | Woehr et al. ................... 604/500 |
| 2013/0184541 A1* | 7/2013 | Antonio et al. ............... 600/309 |

* cited by examiner

*Primary Examiner* — Nicholas Lucchesi
*Assistant Examiner* — Gerald Landry, II
(74) *Attorney, Agent, or Firm* — Jeanne Lukasavage; Craig Metcalf; Kirton McConkie (57) ABSTRACT

An intravenous catheter device is provided which includes a catheter adapter having a fluid chamber, a needle adapter being slidably positioned within the fluid chamber, the needle adapter supporting a base of an introducer needle and a terminal end of a section of intravenous tubing such that a fluid pathway of the introducer needle is in fluid communication with a fluid pathway of the section of intravenous tubing. Following catheterization, the needle adapter is slid to a preferred proximal position whereby a sharpened tip of the introducer needle is shielded within a catheter of the intravenous catheter device, or a portion of the fluid chamber of the catheter adapter. When in the preferred proximal position, fluid communication between the catheter and a section of intravenous tubing is facilitated via the hollow body of the introducer needle.

18 Claims, 8 Drawing Sheets

OVER-THE-NEEDLE INTRAVENOUS CATHETER ASSEMBLY WITH INTEGRATED INTRAVENOUS TUBING

BACKGROUND OF THE INVENTION

This disclosure relates generally to intravenous catheters. More specifically, this disclosure discusses an intravenous catheter device having an integrated introducer needle and intravenous tubing, wherein following catheterization intravenous access is facilitated between the catheter and the intravenous tubing via the hollow body of the introducer needle.

Generally, vascular access devices are used for communicating fluid with the vascular system of patients. For example, catheters are used for infusing fluid (e.g., saline solution, medicaments, and/or total parenteral nutrition) into a patient, withdrawing fluids (e.g., blood) from a patient, and/or monitoring various parameters of the patient's vascular system.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a venipuncture needle coupled to a needle assembly that helps guide the needle and facilitates its cooperation with the catheter. At least the inner surface of the distal portion of the catheter tightly engages the outer surface of the needle to prevent peelback of the catheter and, thereby, to facilitate insertion of the catheter into the blood vessel. The catheter and the introducer needle are often assembled so that the sharp distal tip of the introducer needle extends beyond the distal tip of the catheter. Moreover, the catheter and needle are often assembled so that during insertion, the bevel of the needle faces up, away from the patient's skin. The catheter and introducer needle are generally inserted at a shallow angle through the patient's skin into a blood vessel.

Following catheterization, the introducer needle is withdrawn from the catheter and disposed. The clinician then connects a syringe or section of intravenous tubing to the catheter to access the vasculature of the patient. The clinician must act quickly so as to prevent undesirable exposure to the patient's blood following removal of the introducer needle. In some instances, the clinician occludes or blocks blood flow through the catheter by applying physical pressure to the catheterized vein of the patient. In addition to causing discomfort to the patient, physical occlusion of the patient's vein requires the constant use of one of the clinician's hands, thereby requiring that the clinician attach the syringe or intravenous tubing to the inserted catheter using only one hand. Alternatively, the clinician may solicit the assistance of another clinician, however assistance is not always available. Accordingly, there is a need in the art for a device which overcomes the difficulties and shortcomings associated with currently available technologies. The present disclosure discusses such a device.

BRIEF SUMMARY OF THE INVENTION

The present invention provides an intravenous catheter device having an integrated introducer needle and intravenous tubing, wherein following catheterization intravenous access is facilitated between the catheter and the intravenous tubing via the hollow body of the introducer needle. In some implementations, an intravenous catheter assembly is provided which includes a catheter adapter having a fluid chamber in which is slidably housed a needle adapter. The needle adapter is configured to support a base of an introducer needle and a terminal end of a section of intravenous tubing such that a fluid pathway of the introducer needle is in fluid communication with a pathway of the section of intravenous tubing. The introducer needle further includes a sharpened tip which is positioned distally beyond a tip of a catheter which is coupled to a distal end of the catheter adapter. As such, the sharpened tip of the introducer needle is exposed externally to the catheter to assist in inserting the catheter into the vasculature of the patient.

In some instances, the catheter adapter further includes a septum interposed between an inner surface of the catheter adapter and an outer surface of the introducer needle, wherein the septum divides the fluid chamber of the catheter adapter into a distal fluid chamber and a proximal fluid chamber. In these instances, the septum prevents fluid communication between the distal and proximal fluid chambers.

In some implementations of the present invention, the needle adapter is slidably positioned within the fluid chamber of the catheter adapter between a distal position and a preferred proximal position. When in the distal position, a sharpened tip of the introducer needle is exposed distally beyond a tip of the catheter. When in the preferred proximal position, the introducer needle is withdrawn into the catheter thereby shielding the sharpened tip of the introducer needle within the catheter. In some instances, the preferred proximal position of the needle adapter results in the sharpened tip of the introducer needle being positioned or located in the distal fluid chamber. When in the preferred proximal position, fluid communication between the catheter and the section of intravenous tubing is facilitated through the hollow body of the introducer needle.

In some instances, the interior surface of the catheter adapter further comprises distal and proximal stops to retain the needle adapter in the distal and preferred proximal positions. For example, in some implementations the distal and proximal stops include an annular ridge or indentation which is configured to engage a portion of the needle adapter. In other implementations, the distal and proximal stops include a catch or a clip which is configured to engage a portion of the needle adapter. In some instances, the needle adapter defeats or otherwise bypasses the distal stop when the section of intravenous tubing is pulled by the user in a proximal direction. Furthermore, the needle adapter engages the proximal stop when the section of intravenous tubing is further pulled by the user in a proximal direction. In some instances, the catheter adapter further includes a biasing element which is interposed between the needle adapter and an interior surface of the catheter adapter, wherein the biasing element biases the needle adapter in a proximal direction following catheterization.

BRIEF DESCRIPTION OF THE SEVERAL VIEWS OF THE DRAWINGS

In order that the manner in which the above-recited and other features and advantages of the invention are obtained and will be readily understood, a more particular description of the invention briefly described above will be rendered by reference to specific embodiments thereof, which are illustrated in the appended drawings. Understanding that these drawings depict only typical embodiments of the invention and are not, therefore, to be considered to be limiting of its scope, the invention will be described and explained with additional specificity and detail through the use of the accompanying drawings in which.

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the accompanying Figures, could be arranged and designed in a wide variety of different configurations. Thus, the following more detailed description of some embodiments of the invention, as represented in the Figures, is not intended to limit the scope of the invention, as claimed, but is merely representative of some presently preferred embodiments of the invention.

Generally, the present invention relates to an intravenous catheter device, such as a standard over-the-needle intravenous catheter, which includes an integrated introducer needle and intravenous extension tubing. Unlike traditional catheter devices, the present invention does not require an additional step of coupling or attaching intravenous extension tubing to the catheter following catheterization. The present invention also does not require the step of removing and properly disposing of the needle assembly following venipuncture. Rather, the intravenous catheter devices of the present invention provide an integrated, unitary catheter device which allows a user immediate access to the vasculature of the patient via intravenous tubing, following catheterization.

Figure 1:
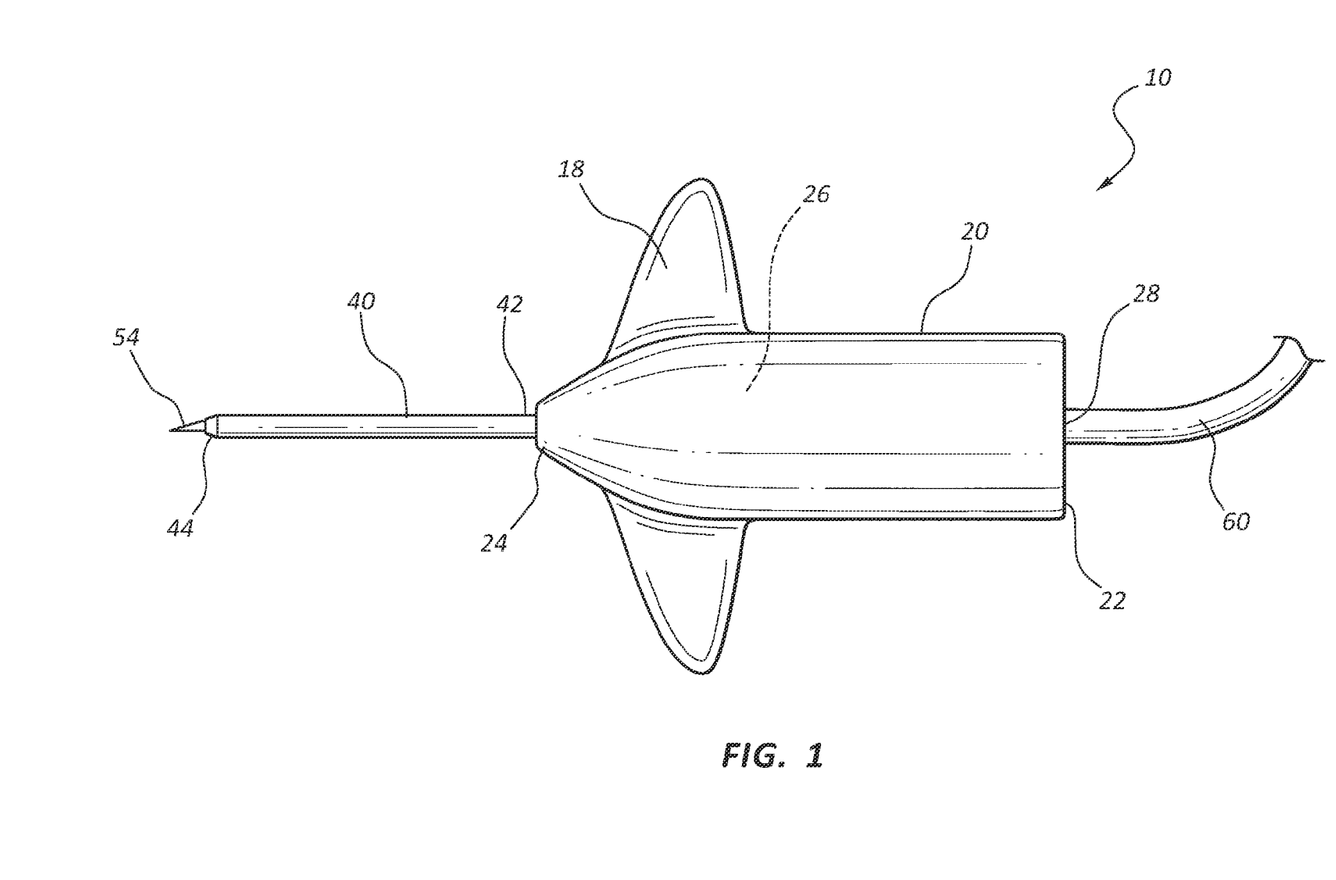
FIG. 1 illustrates a top plan view of an intravenous catheter device in accordance with a representative embodiment of the present invention.

Referring now to FIG. 1, an intravenous catheter device 10 is shown. Intravenous catheter device 10 generally comprises a catheter adapter 20 having a proximal end 22, a distal end 24, and a fluid chamber 26 extending therebetween. Catheter adapter 20 generally comprises a rigid or semi-rigid biocompatible material. For example, in some embodiments catheter adapter 20 comprises a thermoplastic material, such as polyvinyl chloride, polyethylene, polycarbonate or polyurethane material. Catheter adapter 20 may further comprise a thermoset polymer material. In some embodiments, catheter adapter 20 further comprises lateral securement platforms 18 which are provided to assist in handling and securing an intravenous catheter device 10 to a patient during a catheterization procedure.

Distal end 24 is configured to house a proximal end 42 of a catheter 40. Catheter 40 further comprises a tip 44 which is positioned opposite of proximal end 42. In some embodiments tip 44 is tapered so as to provide a smooth transition between a sharpened tip 54 of an introducer needle 50 and catheter 40. The tapered structure of tip 44 facilitates insertion of catheter 40 during catheterization procedures.

Catheter 40 generally comprises an intravenous catheter which includes a biocompatible material, such as a polymer or metallic material. In some embodiments, catheter 40 comprises a flexible polymer material, such as silicon rubber, latex, and/or various thermoplastic elastomers. Catheter 40 may further comprise a rigid polymer or metallic material, as may be desirable for an intended use.

The length and diameter of catheter 40 is generally determined by the application or use for which the intravenous catheter device 10 is intended. Accordingly, one having skill in the art will appreciate that catheter 40 may be modified or adjusted to include any size and dimensions as may be desired or necessary to facilitate a desired use.

Proximal end 22 further comprises an opening 28 through which a section of intravenous tubing 60 is slidably inserted. In some embodiments, the diameter of opening 28 is selected so as to form a fluid tight seal between opening 28 and the outer surface of tubing 60. Opening 28 may further include a gasket or O-ring whereby to form a seal with tubing 60. In other embodiments, the diameter of opening 28 is selected so as to provide minimal tolerance between opening 28 and tubing 60 without restricting movement of tubing 60 through opening 28.

Figure 2A:
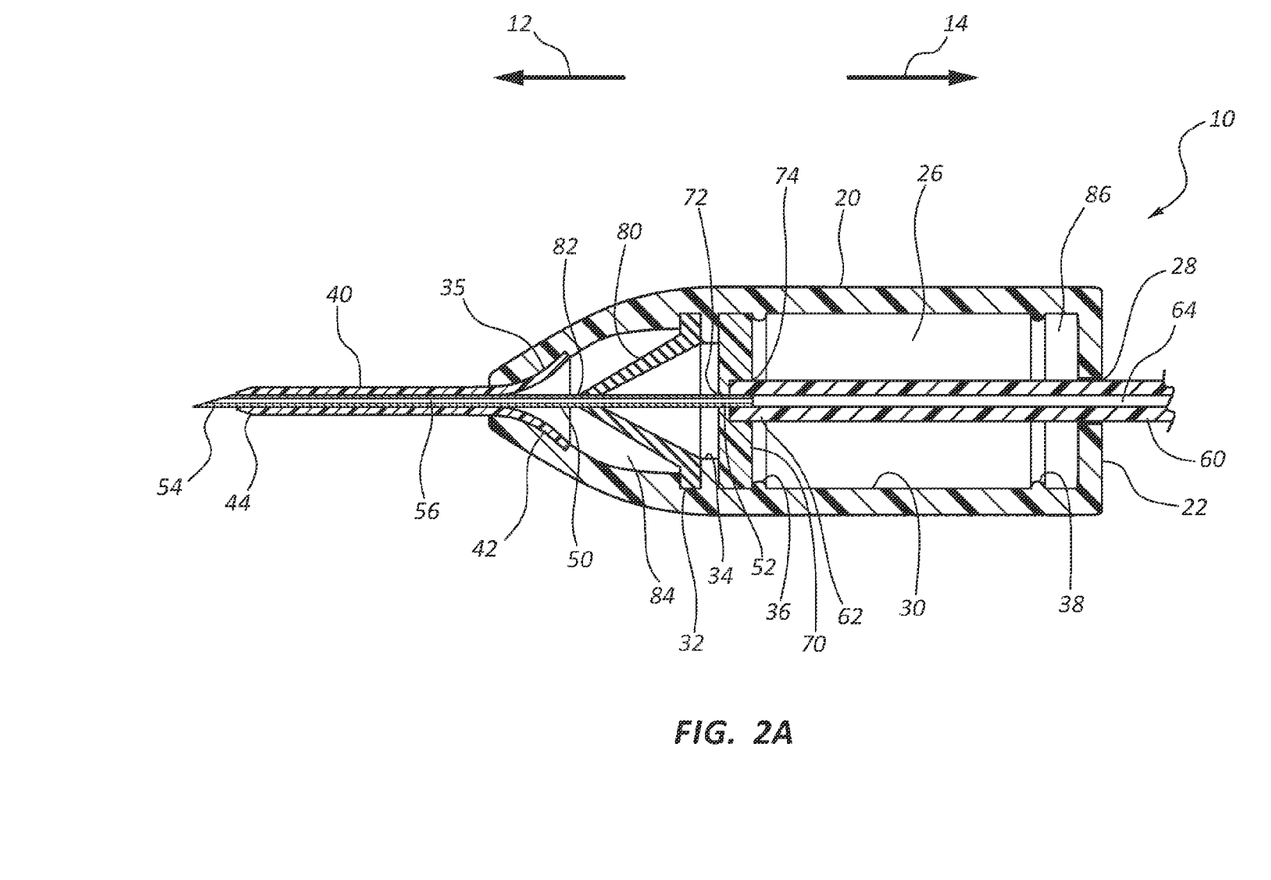
FIG. 2A illustrates a cross-section view of an intravenous catheter device prior to catheterization in accordance with a representative embodiment of the present invention.

Referring now to FIG. 2A, a cross-section side view of an intravenous catheter device 10 is shown. In some embodiments, intravenous catheter device 10 further comprises a needle adapter 70 which is slidably positioned within a fluid chamber 26 of catheter adapter 20. Fluid chamber 26 is generally defined as the hollow interior of catheter adapter 20. In some embodiments, fluid chamber 26 includes various features formed on the inner wall surface 30 of catheter adapter 20. For example, in some embodiments inner wall surface 30 comprises a channel 32 in which is housed a portion of a septum 80. Inner wall surface 30 may further comprise an interior flange 34 provided to prevent or limit movement of needle adapter 70 and a distal direction 12. Inner wall surface 30 may further include a recessed surface 35 for receiving and securing catheter 40 to catheter adapter 20. In some embodiments, catheter 40 may further be secured to catheter adapter 20 via a swaged connector 16 (see FIG. 3, below), wherein catheter 40 is wedged between the swaged connector and the inner surface of catheter adapter 20. Further still, inner wall surface 30 may include a distal stop 36 and a proximal stop 38 which are provided to temporarily maintain distal and proximal positions of the needle adapter 70 within fluid chamber 26, as discussed below.

In some embodiments, needle adapter 70 comprises a distal aperture 72 configured to house a base portion 52 of introducer needle 50. Needle adapter 70 further comprises a proximal aperture 74 configured to house a terminal end 62 of intravenous tubing 60. Base portion 52 and terminal end 62 are fixedly secured to needle adapter 70 such that introducer needle 50, intravenous tubing 60, and needle adapter 70 form a unitary structure. Base portion 52 and terminal end 62 are further secured to needle adapter 70 such that a fluid pathway or hollow body 56 of introducer needle 50 is in fluid communication with a fluid pathway 64 of intravenous tubing 60. Thus, a fluid which enters introducer needle 50 via a sharpened tip 54 flows through a fluid pathway 56 and into a fluid pathway 64 via needle adapter 70.

In some embodiments, needle adapter 70 is secured to a middle portion of introducer needle 50 such that base portion 52 extends proximally past needle adapter 70, rather than terminating within a portion of needle adapter 70. In these instances, base portion 52 is coupled to terminal end 62 at a position without needle adapter 70. For example, base portion 52 and terminal end 62 may be coupled in a fluid tight manner via a crimp or other mechanical connection. In other embodiments, needle adapter 70 is secured to a middle portion of intravenous tubing 60 such that base portion 52 is positioned distally past needle adapter 70, rather than terminating within a portion of needle adapter 70. In these instances, base portion 52 is coupled to terminal end 62 at a position without needle adapter 70.

In some instances, needle adapter 70 comprises a portion of terminal end 62, wherein terminal end 62 performs a dual function of housing base portion 52 and interfacing with inner wall surface 30 of catheter adapter 20. In other instances, needle adapter 70 comprises a portion of base portion 52, wherein base portion 52 performs a dual function of housing terminal end 62 and interfacing with inner wall surface 30 of catheter adapter 20.

Prior to catheterization, needle adapter 70 is positioned within fluid chamber 26 at a maximum distal position such that sharpened tip 54 of introducer needle 50 is exposed distally beyond tip 44 of catheter 40. Accordingly, the position of interior flange 34 is selected to provide the optimal exposure of sharpened tip 54 beyond tip 44. Alternatively, in some embodiments the length of introducer needle 50 is selected to provide the optimal exposure of sharpened tip 54 beyond tip 44 when needle adapter 70 is positioned within fluid chamber 26 at a maximum distal position. Further still, the length of catheter 40 may be selected to provide the optimal exposure of sharpened tip 54 beyond tip 44 when needle adapter 70 is positioned within fluid chamber 26 at a maximum distal position.

In some embodiments, distal stop 36 is provided to temporarily maintain the maximum distal position of needle adapter 70 during the catheterization procedure. Distal stop 36 may include any feature which prevents movement of needle adapter 70 in a proximal direction 14 during catheterization. Thus, distal stop 36 prevents premature sheathing of sharpened tip 54 within catheter 40 during catheterization caused by contact between sharpened tip 54 and the patient.

In some embodiments, distal stop 36 comprises an annular ring formed on inner surface 30. In other embodiments, distal stop 36 comprises a plurality of bumps or intermittent raised surfaces formed on inner surface 30. Distal stop 36 may further include a mechanical or friction interface between needle adapter 70 and inner wall surface 30, wherein a shear force between needle adapter 70 and distal stop 36 is greater than the compressive force between sharpened tip 54 and the patient.

In some embodiments, catheter adapter 20 further comprises a septum 80 disposed within fluid chamber 26 and having an aperture or hole 82 through which introducer needle 50 is inserted. In some embodiments, septum 80 comprises an elastomeric polymer material which is impervious to fluids. In other embodiments, septum 80 comprises a non-elastomeric material having tight tolerances between hole 82 and introducer needle 50. In some embodiments, hole 82 forms a fluid tight seal around introducer needle 50 thereby dividing fluid chamber 26 into a distal fluid chamber 84 and a proximal fluid chamber 86. Thus, a fluid within distal fluid chamber 84 is prevented from bypassing septum 80 into proximal fluid chamber 86.

In some instances, introducer needle 50 is capable of translating or sliding within hole 82 as needle adapter 70 is slid in proximal direction 14. In other instances, the mechanical interface between hole 82 and introducer needle 50 prevents introducer needle 50 from sliding within hole 82, thereby causing septum 80 to collapse and fold as introducer needle is moved in proximal direction 14, as shown in FIG. 2B.

Figure 2B:
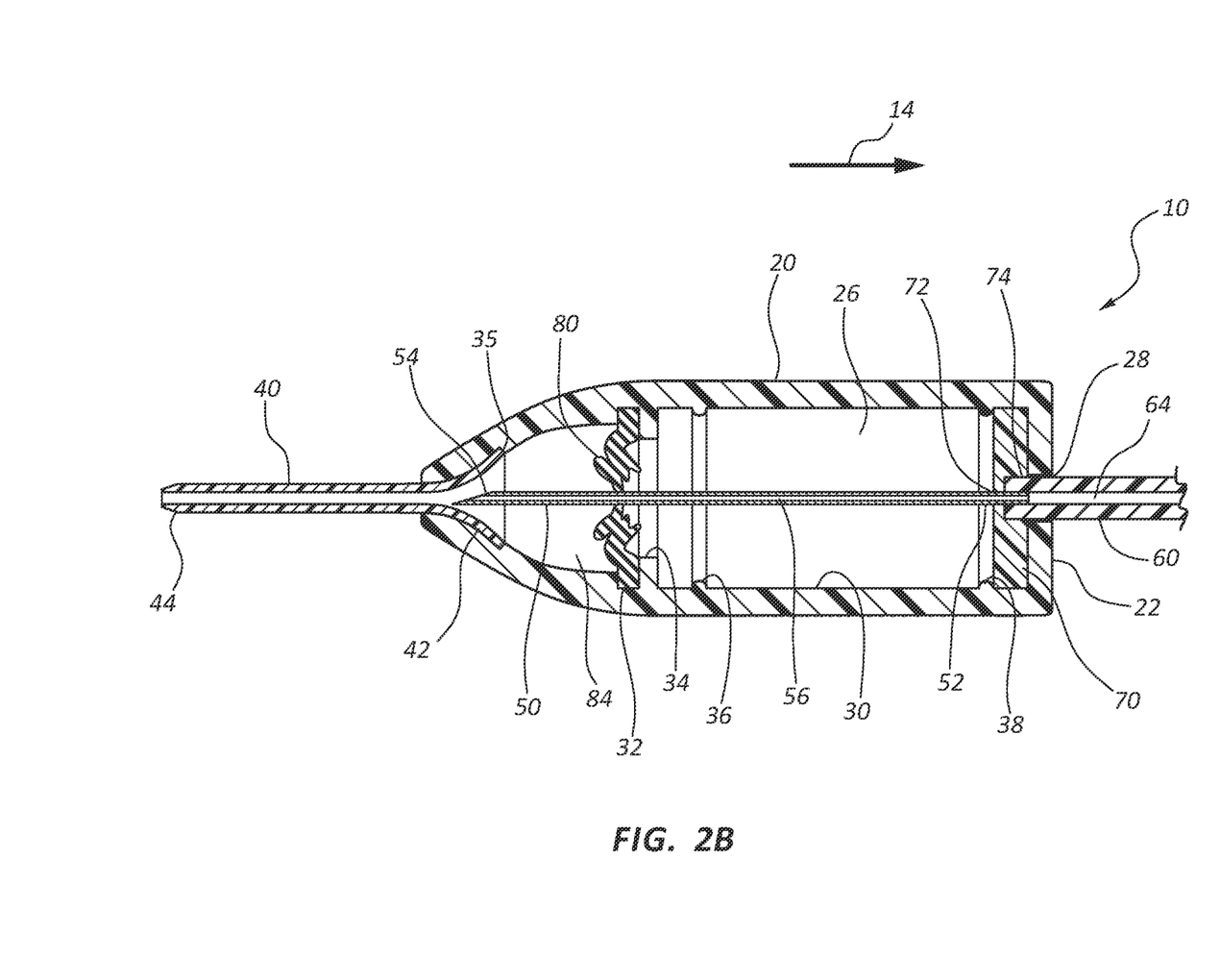
FIG. 2B illustrates a cross-section view of an intravenous catheter device following catheterization in accordance with a representative embodiment of the present invention.

Referring now to FIG. 2B, following catheterization needle adapter 70 is moved in proximal direction 14 thereby withdrawing introducer needle 50 from catheter 40 and shielding sharpened tip 54 within distal fluid chamber 84. In some embodiments, needle adapter 70 is moved or slid in proximal direction 14 as intravenous tubing 60 is pulled in proximal direction 14 by the user. Needle adapter 70 bypasses distal stop 36, if present, as the pulling force exerted on intravenous tubing 60 in proximal direction 14 exceeds a shear force between needle adapter 70 and distal stop 36. Once freed from distal stop 36, needle adapter 70 travels through catheter adapter 20 towards proximal end 22. At a preferred proximal position, needle adapter 70 is secured by proximal stop 38, if present. In some embodiments, the preferred proximal position is determined by a desired position of sharpened tip 54 of introducer needle 50.

For example, in some embodiments the preferred proximal position of needle adapter 70 results in sharpened tip 54 being positioned within distal fluid chamber 84, wherein distal fluid chamber 84 is separated from proximal fluid chamber 86 via septum 80. Accordingly, fluid flows between catheter 40 and intravenous tubing 60 via distal fluid chamber 84 and introducer needle 50. In other embodiments, the preferred proximal position of needle adapter 70 results in sharpened tip 54 being positioned within a proximal portion of catheter 40, as shown in FIG. 3.

Figure 3:
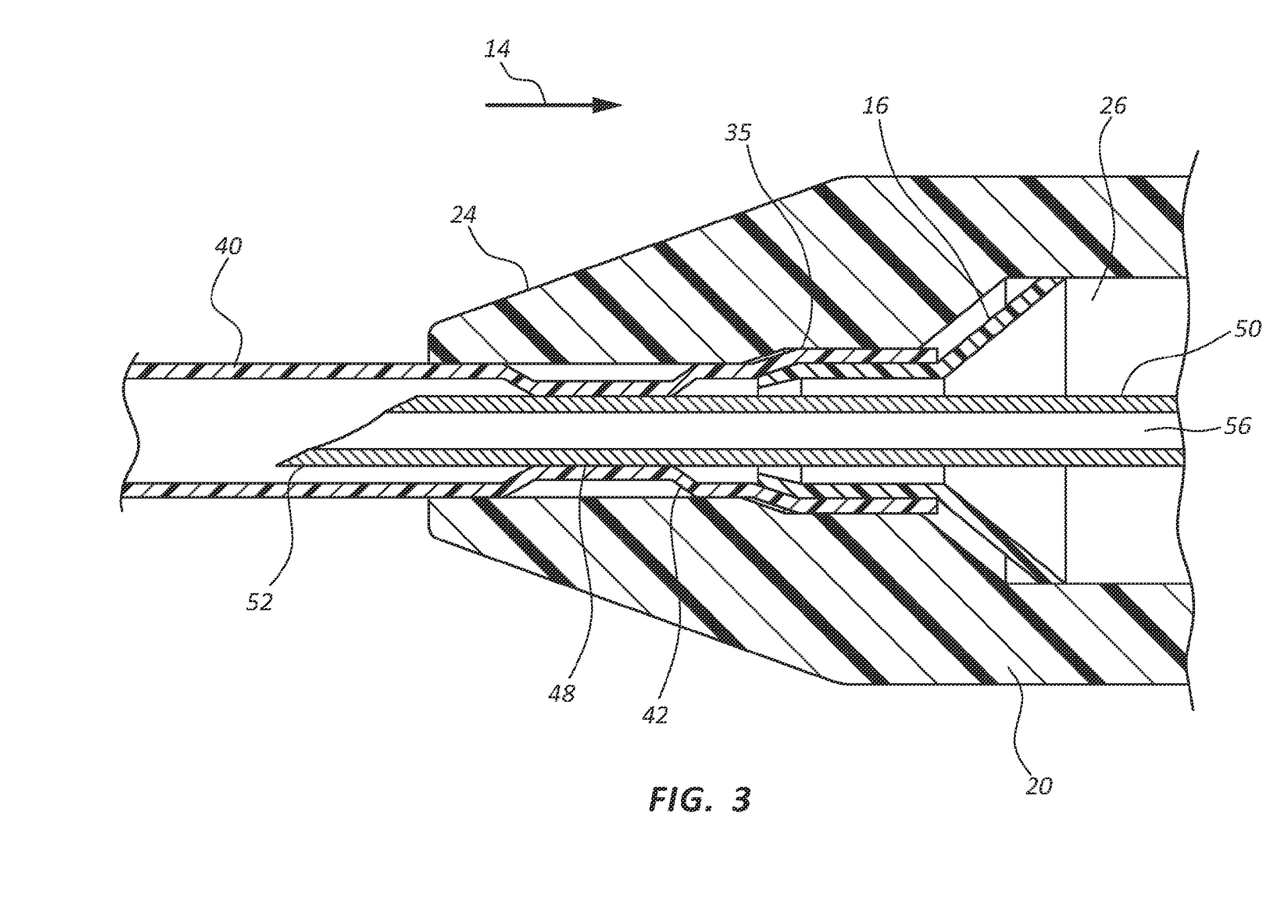
FIG. 3 illustrates a detailed view of an intravenous catheter device comprising a catheter having a reduced inner diameter in accordance with a representative embodiment of the present invention.

With continued reference to FIG. 3, in some embodiments catheter 40 comprises a proximal end 42 having a reduced inner diameter 48 which forms a fluid tight seal with the outer surface of introducer needle 50. As such, fluid communication between catheter 40 and intravenous tubing 60 is facilitated by introducer needle 50, wherein reduced inner diameter 48 prevents fluid from passing between catheter 40 and outer surface of introducer needle 50 and into fluid chamber 26 of catheter adapter 20. Thus, the preferred proximal position of needle adapter 70 is determined by the distal position of sharpened tip 54 with respect to reduced inner diameter 48 of catheter 40. Accordingly, some embodiments of the present invention do not require a septum to divert fluid flow between catheter 40 and intravenous tubing 60 via introducer needle 50. Rather, a fluid tight seal between introducer needle 50 and the inner surface of catheter 40 provides the desired diversion of fluid through introducer needle 50.

Figure 4A:
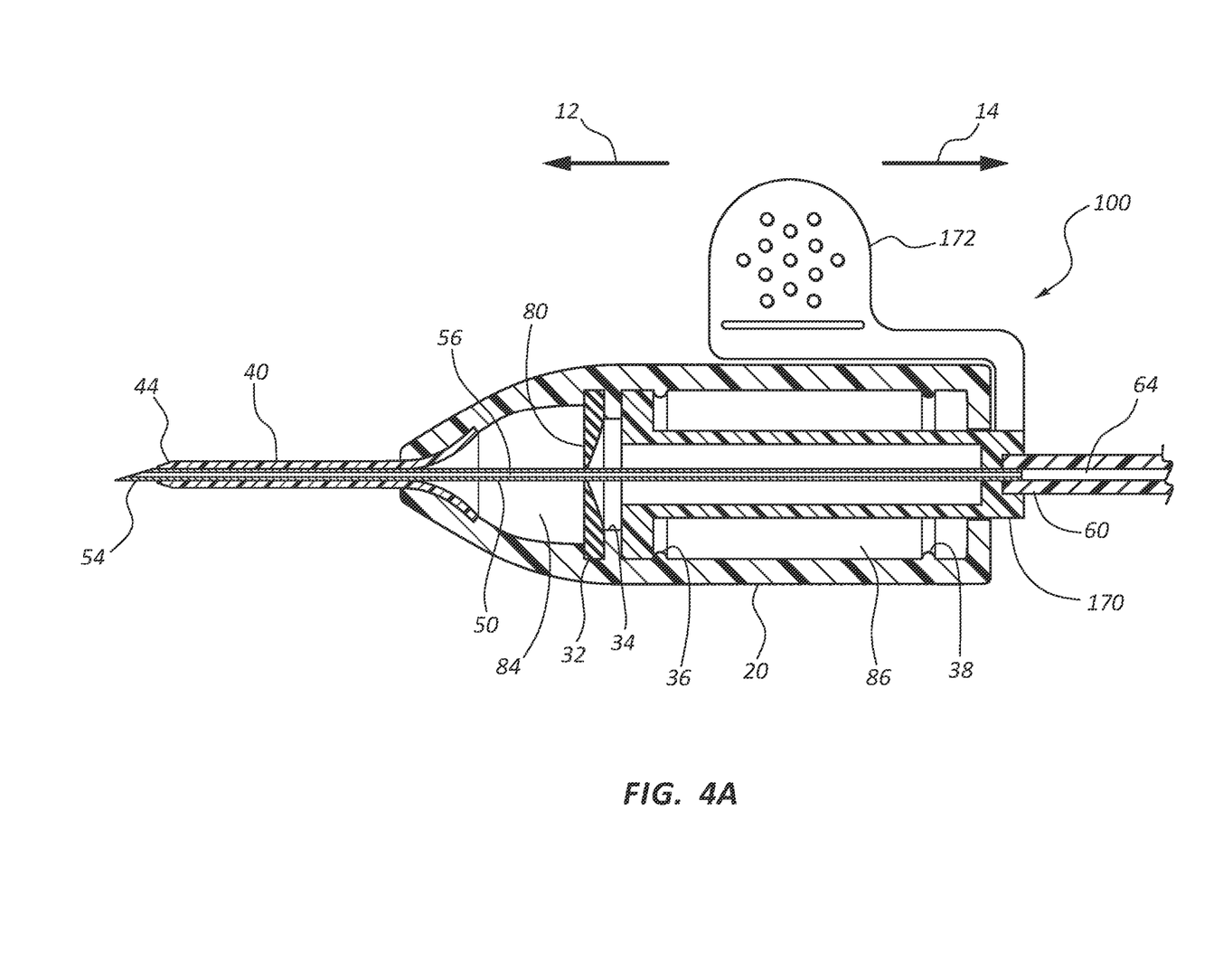
FIG. 4A illustrates a cross-section view of an intravenous catheter device having a paddle grip prior to catheterization in accordance with a representative embodiment of the present invention.

Referring now to FIG. 4A, a cross-section top view of an intravenous catheter device 100 is shown. In some embodiments, intravenous catheter device 100 comprises a needle adapter 170 having an integrated paddle grip 172 which is positioned external to catheter adapter 20. Paddle grip 172 is provided as a means for gripping intravenous catheter device 100 during catheterization. For example, in some embodiments paddle grip 172 is gripped between the thumb and opposing finger of the user to control device 100 during catheterization. In some instances, the distal position of needle adapter 170 is maintained by distal stop 36. In other instances, the forward or distal position of needle adapter 170 is maintained via the user's contact with paddle grip 172 during insertion of sharpened tip 54 of introducer needle 50 into the patient.

In particular, when device 100 is held by paddle grip 172 and advanced in distal direction 12, the interconnected relationship between introducer needle 50 and needle adapter 170 prevents movement of needle adapter 170 in proximal direction 14 relative to catheter 40 and catheter adapter 20 when sharpened tip 54 contacts the surface of the patient. Thus, paddle grip 172 prevents premature shielding of sharpened tip 54 within catheter 40 during catheterization. Following catheterization, paddle grip 172 is moved in proximal direction 14, thereby withdrawing sharpened tip 54 into catheter 40, as shown in FIG. 4B.

Figure 4B:
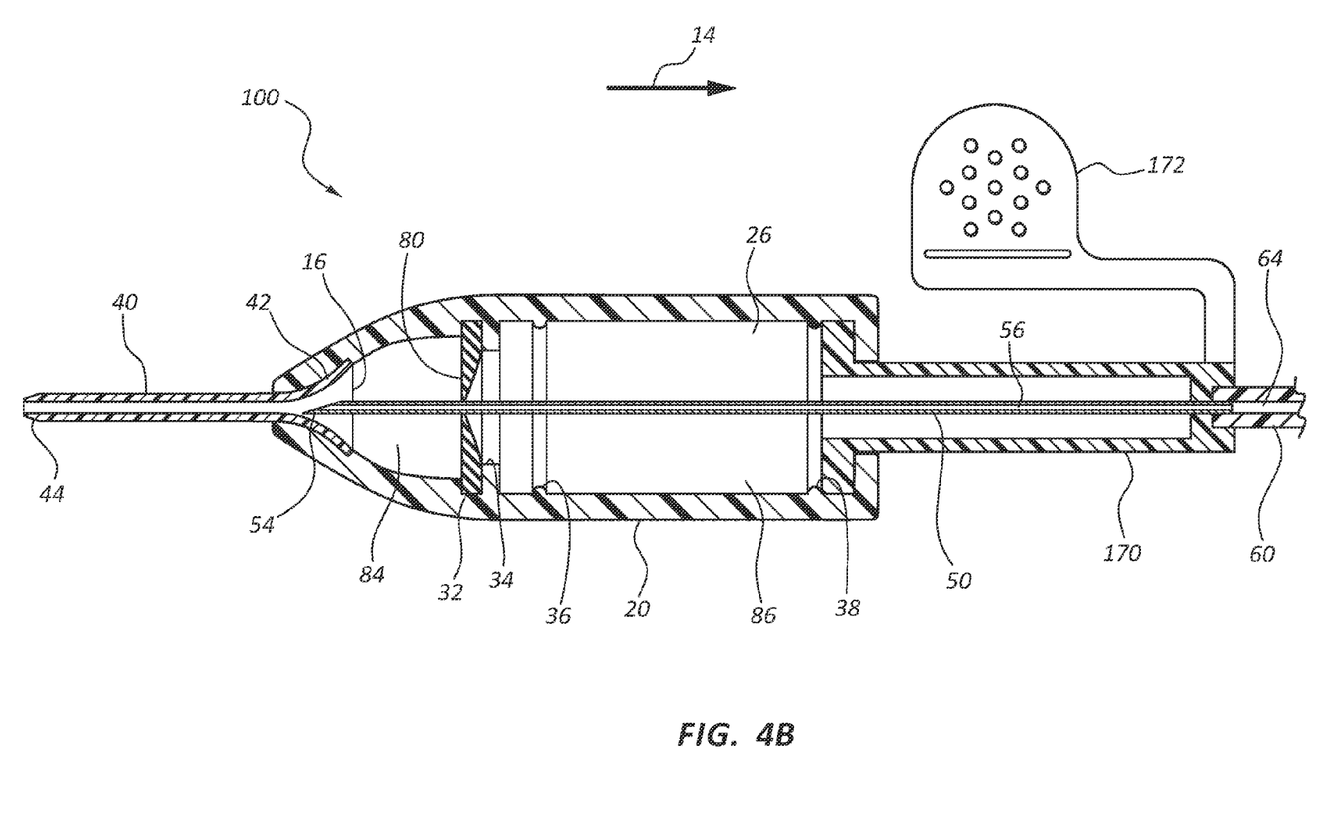
FIG. 4B illustrates a cross-section view of an intravenous catheter device having a paddle grip following catheterization in accordance with a representative embodiment of the present invention.

Referring now to FIG. 4B, intravenous catheter device 100 is configured to permit movement of needle adapter 170 from a distal position to a preferred proximal position following catheterization. When in the preferred proximal position, sharpened tip 54 of introducer needle 50 is withdrawn proximally into catheter 40 such that sharpened tip 54 is shielded. In some embodiments, the preferred proximal position of needle adapter 170 results in sharpened tip 54 being positioned within a proximal portion 42 of catheter 40, wherein a fluid tight seal is formed between the outer surface of introducer needle 50 and an inner surface of catheter 40. In other embodiments, the preferred proximal position of needle adapter 170 results in sharpened tip 54 being positioned within distal fluid chamber 84, wherein fluid communication between catheter 40 and intravenous tubing 60 is facilitated via introducer needle 50. In some embodiments, catheter adapter 20 further comprises a septum 80 which prevents fluid communication between distal fluid chamber 84 and proximal fluid chamber 86. As such, fluid must travel through introducer needle 50 following catheterization.

Figure 5A:
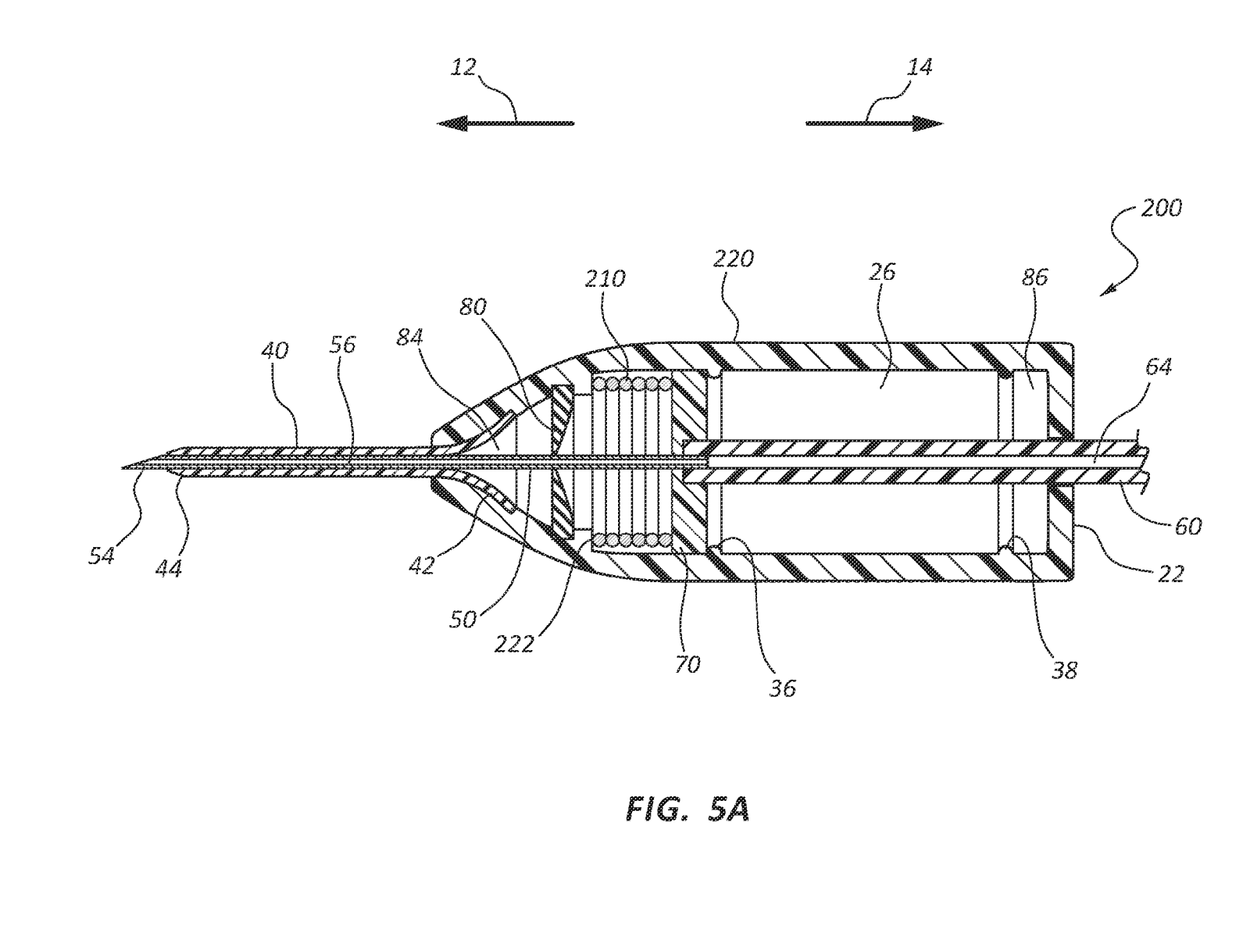
FIG. 5A illustrates a cross-section view of an intravenous catheter device having a biasing element prior to catheterization in accordance with a representative embodiment of the present invention.

Referring now to FIG. 5A, in some embodiments an intravenous catheter device 200 is provided which includes a biasing element 210 to assist in moving needle adapter 70 from a distal position to a preferred proximal position following catheterization. Biasing element 210 generally comprises a resilient member which is interposed between a distal surface of needle adapter 70 and an inner surface 222 of catheter adapter 220, such that when catheter adapter 70 is in a distal position, biasing member 210 applies a force upon needle adapter 70 in proximal direction 14. For example, in some embodiments biasing element 210 comprises an open coil spring having a first end in contact with inner surface 222 and a second end in contact with needle adapter 70. Biasing element 210 may further include an elastomeric polymer, a compression spring, a conical compression spring, a magazine spring, or other device or material which is capable of exerting a proximal force on needle adapter 70, in accordance with the teachings of the present invention. In some embodiments, biasing element 210 is positioned external to catheter adapter 20 (not shown), wherein biasing element 210 is interposed between an external, proximal end of needle adapter 70 (as in configuration depicted in FIGS. 4A and 4B) and an outer surface of catheter adapter 220.

In some embodiments, a distal position of needle adapter 70 is selected such that sharpened tip 54 of introducer needle 50 is exposed distally beyond tip 44 of catheter 40. This distal position of needle adapter 70 is maintained by distal stop 36. Thus the proximal force exerted upon needle adapter 70 by biasing member 210 is less than the shear force between needle adapter 70 and distal stop 36. Further, the shear force between needle adapter 70 and distal stop 36 is greater than the compressive force between sharpened tip 54 and the surface of the patient during catheterization. As such, premature shielding of sharpened tip 54 within catheter 40 is prevented during catheterization.

In some instances, distal stop 36 is deactivated and thereby releases needle adapter 70 upon the user pushing a button or trigger (not shown) located on the external surface of catheter adapter 20. Upon deactivation, biasing member 210 automatically slides or biases needle adapter 70 in proximal direction 14. Proximal stop 38 then engages needle adapter 70 in the preferred proximal position. Thus, some embodiments of the present invention provide for automated relocation of needle adapter 70 from the distal position to the preferred proximal position following catheterization.

Figure 5B:
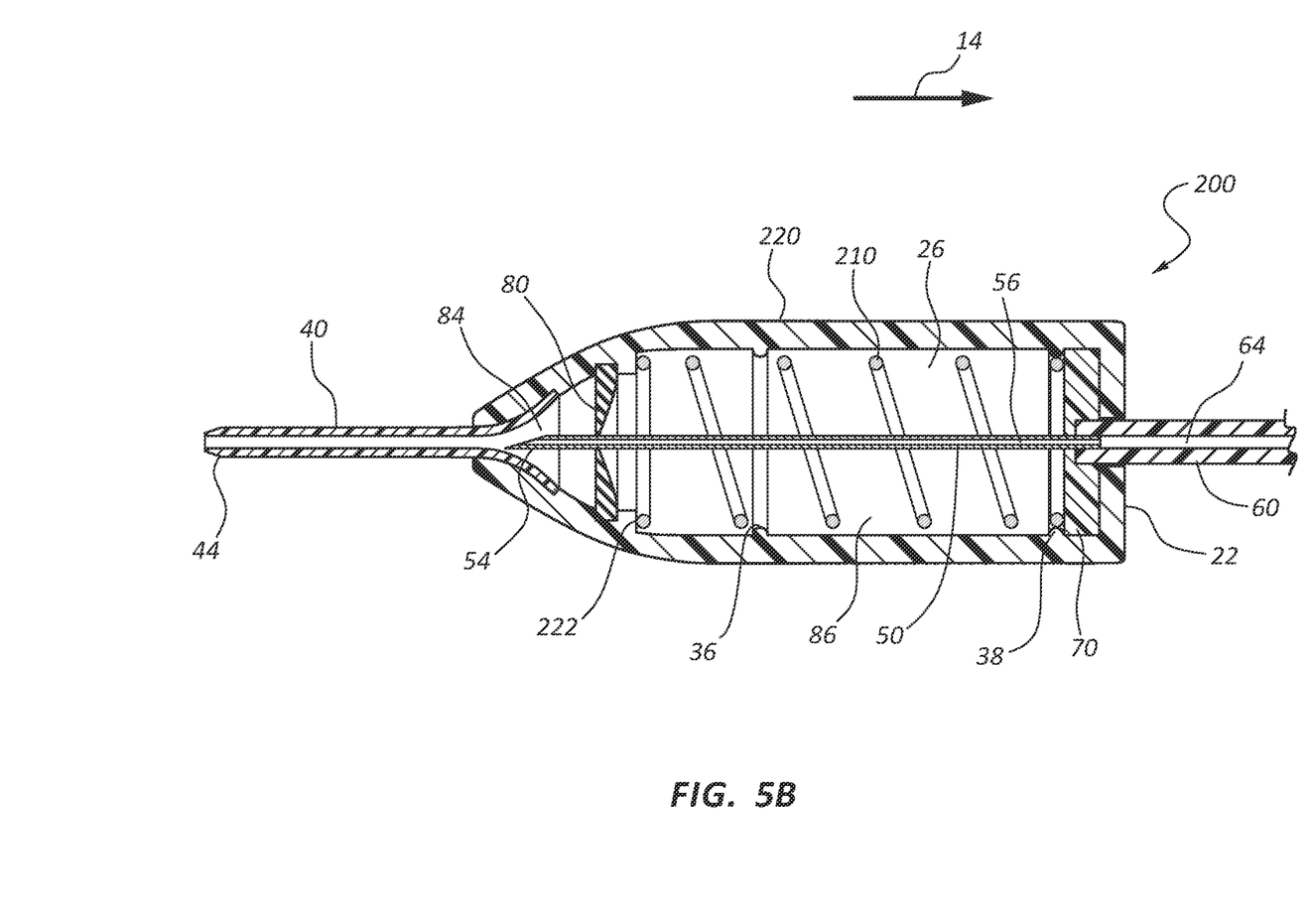
FIG. 5B illustrates a cross-section view of an intravenous catheter device having a biasing element following catheterization in accordance with a representative embodiment of the present invention.

In some embodiments, intravenous tubing 60 is manually pulled in proximal direction 14 following catheterization thereby overcoming the shear force between needle adapter 70 and distal stop 36. As such, needle adapter 70 bypasses distal stop 36. Once clear of distal stop 36, biasing element 210 assists needle adapter 70 in traveling proximally through fluid chamber 26 towards proximal end 22 of needle adapter 220, as shown in FIG. 5B.

In some instances the compressive force of biasing element 210 is sufficient to reposition needle adapter 70 behind proximal stop 38 and into a preferred proximal position, as shown. In other instances a user must pull intravenous tubing 60 in proximal direction 14 to cause needle adapter 72 bypass proximal stop 38 and position needle adapter 70 in the preferred proximal position. Further, in some embodiments proximal stop 38 comprises a catch or clip which is configured to interlock with needle adapter 70 thereby maintaining the preferred proximal position of needle adapter 70 following catheterization.

As discussed previously, in some embodiments the preferred proximal position of needle adapter 70 results in sharpened tip 54 being withdrawn from catheter 40 and positioned within distal fluid chamber 84, wherein septum 80 prevents passage of fluid between distal fluid chamber 84 and proximal fluid chamber 86. As such, fluid communication between a fluid pathway 64 of intravenous tubing 60 and catheter 40 is facilitated via introducer needle 50.

Some embodiments further include a method for assembling or manufacturing an intravenous catheter assembly in accordance with the teachings of the present invention. For example, a method for manufacturing an intravenous catheter assembly may include a first step whereby a catheter adapter is provided having a proximal end, a distal end and a pathway extending therebetween. A catheter may then be coupled to the distal end of the of the catheter adapter, wherein the catheter includes a lumen and a tip. A needle adapter is further provided having a surface for supporting a base end of an introducer needle. The introducer needle generally includes a sharpened end, a base, and a hollow body extending therebetween. For some methods, the base of the introducer needle is coupled to, and supported by the needle adapter. A section of intravenous tubing is further coupled to the needle adapter, wherein the needle adapter facilitates fluid communication between the hollow body of the introducer needle and a fluid pathway of the intravenous tubing. The introducer needle, needle adapter, and section of intravenous tubing are then slidably housed within the lumen of the catheter adapter, in accordance with the teachings above.

The present invention may be embodied in other specific forms without departing from its structures, methods, or other essential characteristics as broadly described herein and claimed hereinafter. All of the described embodiments and examples are to be considered in any and all respects as illustrative only, and not restrictive. The scope of the invention is, therefore, indicated by the appended claims, rather than by the foregoing description. All changes that come within the meaning and range of equivalency of the claims are to be embraced within their scope.

The invention claimed is:

1. An intravenous catheter assembly, comprising:
   a catheter adapter having a proximal end, a distal end and a fluid chamber extending therebetween;
   a catheter coupled to the distal end of the catheter adapter, the catheter having a lumen in fluid communication with the fluid chamber of the catheter adapter;
   a needle adapter slidably positioned within the fluid chamber of the catheter adapter between a distal position and a proximal position, the needle adapter supporting a base end of an introducer needle and a terminal end of a section of intravenous tubing such that a fluid pathway of the introducer needle is in fluid communication with a fluid pathway of the section of intravenous tubing; and
   a septum interposed between an inner surface of the catheter adapter and an outer surface of the introducer needle, wherein the septum divides the fluid chamber into a distal fluid chamber and a proximal fluid chamber, and wherein an inner surface of the catheter adapter further comprises a proximal stop to retain the needle adapter in the proximal position.

2. The assembly of claim 1, wherein the septum prevents passage of a fluid between the distal and proximal fluid chambers.

3. The assembly of claim 1, wherein the distal position results in a sharpened tip of the introducer needle being positioned distally to a tip of the catheter.

4. The assembly of claim 1, wherein the proximal position results in a sharpened tip of the introducer needle being shielded within at least one of the fluid pathway of the catheter and the distal fluid chamber.

5. The assembly of claim 1, wherein the lumen of the catheter is in fluid communication with the fluid pathway of the section of intravenous tubing via the fluid pathway of the introducer needle.

6. The assembly of claim 1, wherein the distal fluid chamber is in fluid communication with the fluid pathway of the section of intravenous tubing via the fluid pathway of the introducer needle.

7. The assembly of claim 1, further comprising a biasing element interposed between an inner surface of the catheter adapter and the needle adapter, the biasing element biasing the needle adapter in a proximal direction from the distal position to the proximal position.

8. The assembly of claim 1, further comprising a biasing element interposed between an outer surface of the catheter adapter and the needle adapter, the biasing element biasing the needle adapter in a proximal direction from the distal position to the proximal position.

9. The assembly of claim 1, wherein an inner surface of the catheter adapter further comprises a distal stop to temporarily retain the needle adapter in the distal position during catheterization.

10. An intravenous catheter assembly, comprising:
    a catheter adapter having a proximal end, a distal end and a pathway extending therebetween, the catheter adapter further having an inner surface comprising a proximal stop;
    a catheter coupled to the distal end of the catheter adapter, the catheter having a lumen, a portion of the lumen having a reduced inner diameter; and
    an introducer needle having a sharpened tip, a base and a hollow body extending therebetween, the introducer needle being slidably positioned within the lumen of the catheter and the pathway of the catheter adapter between a distal position and a proximal position, the sharpened tip of the introducer needle extending distally beyond a tip of the catheter, and an outer surface of the body forming a fluid-tight seal with the reduced inner diameter of the lumen, the fluid-tight seal dividing the lumen of the catheter into a distal fluid chamber and a proximal fluid chamber, wherein the proximal stop is capable of retaining the needle in the proximal position.

11. The assembly of claim 10, further comprising a needle adapter slidably positioned within the pathway between the proximal and distal positions, the needle adapter supporting the base of the introducer needle.

12. The assembly of claim 11, wherein the needle adapter further supports a terminal end of a section of intravenous tubing such that a fluid pathway of the intravenous tubing is in fluid communication with the distal fluid chamber of the catheter via the hollow body of the introducer needle.

13. The assembly of claim 12, wherein the fluid-tight seal diverts fluid within the distal fluid chamber of the catheter through the sharpened tip of the introducer needle, through the body of the introducer needle and through the fluid pathway of the section of intravenous tubing via the needle adapter.

14. The assembly of claim 10, wherein the needle adapter is slidably positioned within the pathway between the distal position and the proximal position, the distal position resulting in the sharpened tip of the introducer needle being exposed distally beyond the tip of the catheter, and the proximal position resulting in the sharpened tip of the introducer needle being shielded within the distal fluid chamber of the catheter.

15. A method for manufacturing an intravenous catheter assembly, comprising:
    providing a catheter adapter having a proximal end, a distal end and a pathway extending therebetween, the catheter adapter further having an inner surface comprising a proximal stop;
    coupling a catheter to the distal end of the catheter adapter, the catheter having a lumen and a tip;
    slidably positioning a needle adapter within the pathway of the catheter adapter between a distal position and a proximal position;
    slidably positioning an introducer needle within the lumen of the catheter and the pathway of the catheter adapter, the introducer needle having a sharpened tip, a base and a hollow body extending therebetween, the base of the introducer needle being supported by the needle adapter, wherein the proximal stop is capable of retaining the needle in the proximal position; and
    coupling a section of intravenous tubing to the needle adapter such that a fluid pathway of the section of intravenous tubing is in fluid communication with the hollow body of the introducer needle.

16. The method of claim 15, wherein the distal position results in the sharpened tip of the introducer needle being exposed distally beyond the tip of the catheter, and the proximal position results in the sharpened tip of the introducer needle being shielded within the lumen of the catheter.

17. The method of claim 16, further comprising a step for disposing a septum within the pathway of the catheter adapter, an opening of the septum forming a fluid-tight seal with an exterior surface of the introducer needle, the septum dividing the pathway into a proximal fluid chamber and a distal fluid chamber.

18. The method of claim 17, wherein the fluid pathway of the section of intravenous tubing is in fluid communication with the distal fluid chamber of the catheter adapter via the introducer needle when the introducer needle is in the proximal position.

* * * * *